CHRYSANTHEMUM PLANT
Filed Aug. 20, 1971
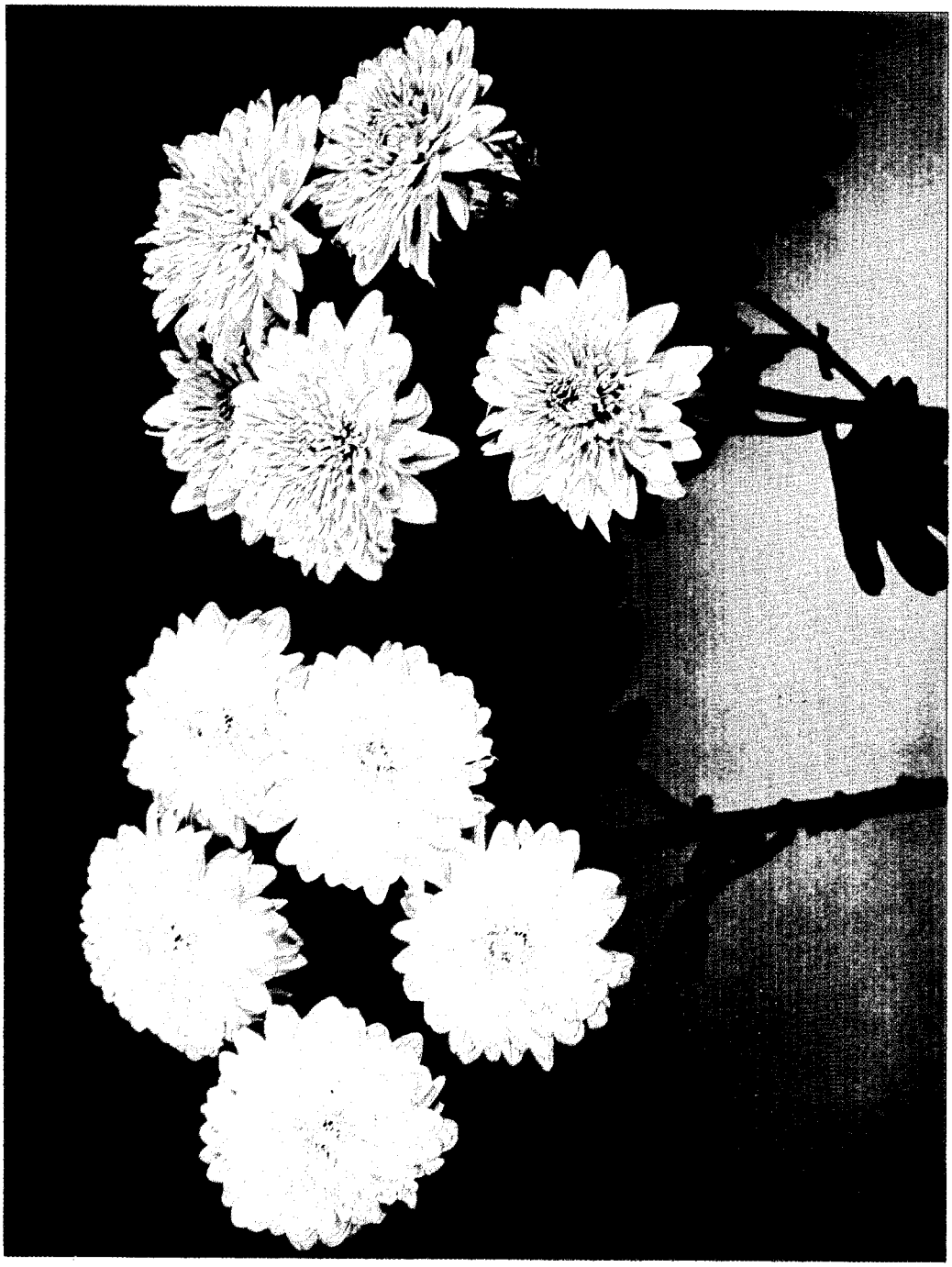

United States Patent Office

Plant Pat. 3,334
Patented May 15, 1973

3,334
CHRYSANTHEMUM PLANT

Percy S. Helveston, Fort Myers, Fla., and Walter H. Jessel, Jr., Doylestown, and William E. Duffett, Akron, Ohio, assignors to Percy S. Helveston, Fort Myers, Fla.

Filed Aug. 20, 1971, Ser. No. 173,704
Int. Cl. A01h *5/00*
U.S. Cl. Plt.—78 1 Claim

The present invention comprises a new and distinct cultivar of chrysanthemum plant which is a sport of the unpatented cultivar known in the United States as Show-Off.

The new cultivar is similar in many respects to Show-Off, having the same characteristics of:

(1) Plant habit.
(2) Decorative flower form.
(3) Flowering response.
(4) Foliage size, shape and color.

The new cultivar is distinguished from Show-Off by the following characteristics:

(1) A yellow color.

weeks, and the following detailed description is based on observations made of the new cultivar in a greenhouse in Barberton, Ohio. The response time, blooming period, color, and total vigor may vary significantly with varying environmental conditions such as temperature, day length, and light intensity.

Suggested flowering in the northern and western United States is from mid-April through October; in coastal California, mid-March through October, and in Florida, mid-December through April.

The accompanying drawing shows the unique characteristics of the new cultivar, the color being as nearly true as possible with color illustrations of this type. In the drawing, the new cultivar appears on the left and the parent cultivar Show-Off on the right.

In the description which follows, color references are made to the Munsell Color Book, 1963 edition, and comparisons are made with the cultivar Show-Off. Where only a single value or description appears for the new cultivar, the same value or description applies to the parent cultivar as well.

BOTANICAL CLASSIFICATION: *Chrysanthemum morifolium*

| | Yellow Show-Off | Show-Off |
|---|---|---|
| Bloom: | | |
| Size | Approximately 2¾″ | Approximately 2½″. |
| Fully expanded | Approximately 3⅜″ | Approximately 3⅛″. |
| Borne | Elongated pedicels | |
| Stems | Strong | |
| Form | Decorative | |
| Permanence | 10–12 days | |
| Color: | | |
| Center of flower | Yellow green, 10Y7/10 | Gold yellow, 1.25Y7/12. |
| Base of petals | Yellow, 7.5Y8.5/8 | Yellow, 7.5Y8.5/8. |
| Inside of petals | Yellow, 7.5Y8.5/12 to 7.5Y9/12 | Gold bronze, 10YR7/10 to golden yellow, 2.5Y8/10. |
| Reverse of petals | Yellow, 7.5Y9/12 | Light yellow, 7.5Y9/6. |
| Tonality from a distance | Yellow | Gold bronze. |
| Discoloration | Yellow, 7.5Y9/12 | Gold, yellow 2.5Y8/10. |
| Petals: | | |
| Texture | Smooth | |
| Appearance and form | Open at base, broadening quickly to wide, flat keel tapering to a blunt point, | |
| Arrangement | Composite, whorled on a single receptacle | |
| Persistence | Resist shatter | |
| Fragrance | Typical chrysanthemum | |
| Reproductive organs: | | |
| Stamen, anthers | None to 35 | None to 15. |
| Pollen | None to scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 40″ when grown as a single stem crop with 2-3 long day weeks and 11–12 weeks total crop time during the various seasons of the year as defined in the timetables published by Yoder Bros., Inc. | |
| Spread | None when grown single stem to slight when pinched | |
| Foliage: | | |
| Top side | Dark green, 7.5GY3/4 | |
| Size | 5½″ to 6½″ long, 3½″ wide | |
| Quantity | Numerous | |
| Shape | Spatulate lobed | |
| Texture | Smooth | |
| Ribs and veins | Prominent | |
| Edge | Deeply indented | |
| Serration | Moderate | |
| Under side | Light green, 7.5GY5/4 | |
| Stipules | Rudimentary | |

(2) Slightly larger flowers.

(3) Fewer ray florets during the low light periods of the year.

(4) Flowers do not mature as rapidly and hold their form longer when flowered in low light periods.

The new cultivar was discovered as a flowering plant at Fort Myers, Fla., and when asexually reproduced by cuttings at Barberton, Ohio has been found to retain its distinctive characteristics through successive propagations.

The new cultivar when grown in the vicinity of Barberton, Ohio, has a response period of approximately 9

We claim:

1. A new and distinct cultivar of chrysanthemum characterized particular as to its uniqueness when compared to the parent cultivar Show-Off by its flowers which are yellow in color and slightly larger, and which do not mature as rapidly and hold their form longer when flowered in low light periods.

No references cited.

ROBERT E. BAGWILL, Primary Examiner